United States Patent

Mizuhata et al.

[11] Patent Number: 5,790,259
[45] Date of Patent: Aug. 4, 1998

[54] REFLECTION-TYPE PHOTOELECTRIC SENSING APPARATUS

[75] Inventors: Shinji Mizuhata; Hayami Hosokawa, both of Kyoto; Arata Nakamura, Osaka; Nobuharu Ishikawa; Hiroyuki Inoue, both of Kyoto; Satoru Shimokawa, Shiga; Masahiro Kurokawa, Osaka; Kohei Tomita; Norimasa Yamanaka, both of Kyoto, all of Japan

[73] Assignee: Omron Corporation, Kyoto, Japan

[21] Appl. No.: 628,257

[22] Filed: Apr. 5, 1996

[30] Foreign Application Priority Data

Apr. 6, 1995 [JP] Japan ................. 7-108072
May 31, 1995 [JP] Japan ................. 7-158384
Nov. 15, 1995 [JP] Japan ................. 7-322153

[51] Int. Cl.$^6$ ............................. G01N 21/55; G01J 4/00
[52] U.S. Cl. ............................. 356/445; 356/369
[58] Field of Search ..................... 356/445, 446, 356/369

[56] References Cited

U.S. PATENT DOCUMENTS 1,949,619  3/1934  Pfund ........................... 356/446
5,139,339  8/1992  Courtney et al. .............. 356/446

FOREIGN PATENT DOCUMENTS 4-369468  12/1992  Japan .

Primary Examiner—Frank G. Font
Assistant Examiner—Amanda Merlino
Attorney, Agent, or Firm—Foley & Lardner

[57] ABSTRACT

Each of a detection sample object and a non-detection sample object is illuminated with S-polarization light, for instance. S-polarization light and P-polarization light reflected from each sample object are detected by different photodetecting elements. Glossiness values and light quantities of the detection and non-detection sample objects are judged based on detection outputs of the photodetecting elements, and a glossiness difference and a light quantity difference are calculated. An evaluation function having at least one of the glossiness and the light quantity as a variable is determined by using the glossiness difference and the light quantity difference. Thresholds for object discrimination are calculated based on evaluation function values of the detection and non-detection sample objects.

3 Claims, 16 Drawing Sheets

FIG. 6A

| GLOSSINESS | WORK | S | P | X = S − P | Y = S + P |
|---|---|---|---|---|---|
| A | WHITE DRAWING SHEET | 70 | 50 | 20 | 120 |
| B | TAPE ON WHITE DRAWING SHEET | 160 | 50 | 110 | 210 |

FIG. 6B

| GLOSSINESS | WORK | S | P | X = S − P | Y = S + P |
|---|---|---|---|---|---|
| A | WHITE, GLOSSY PLASTICS | 160 | 50 | 110 | 210 |
| B | BLACK, GLOSSY PLASTICS | 110 | 2 | 108 | 112 |

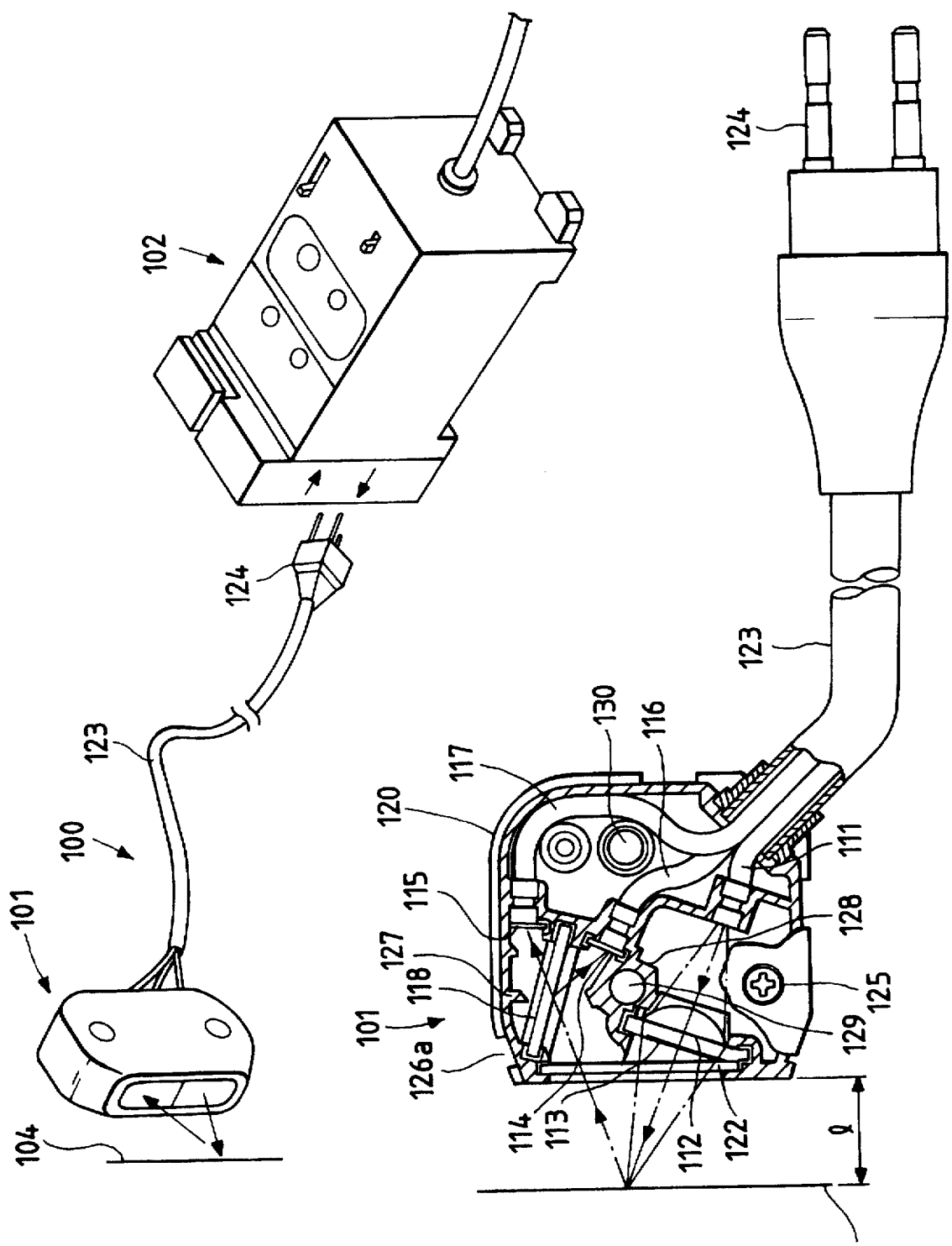

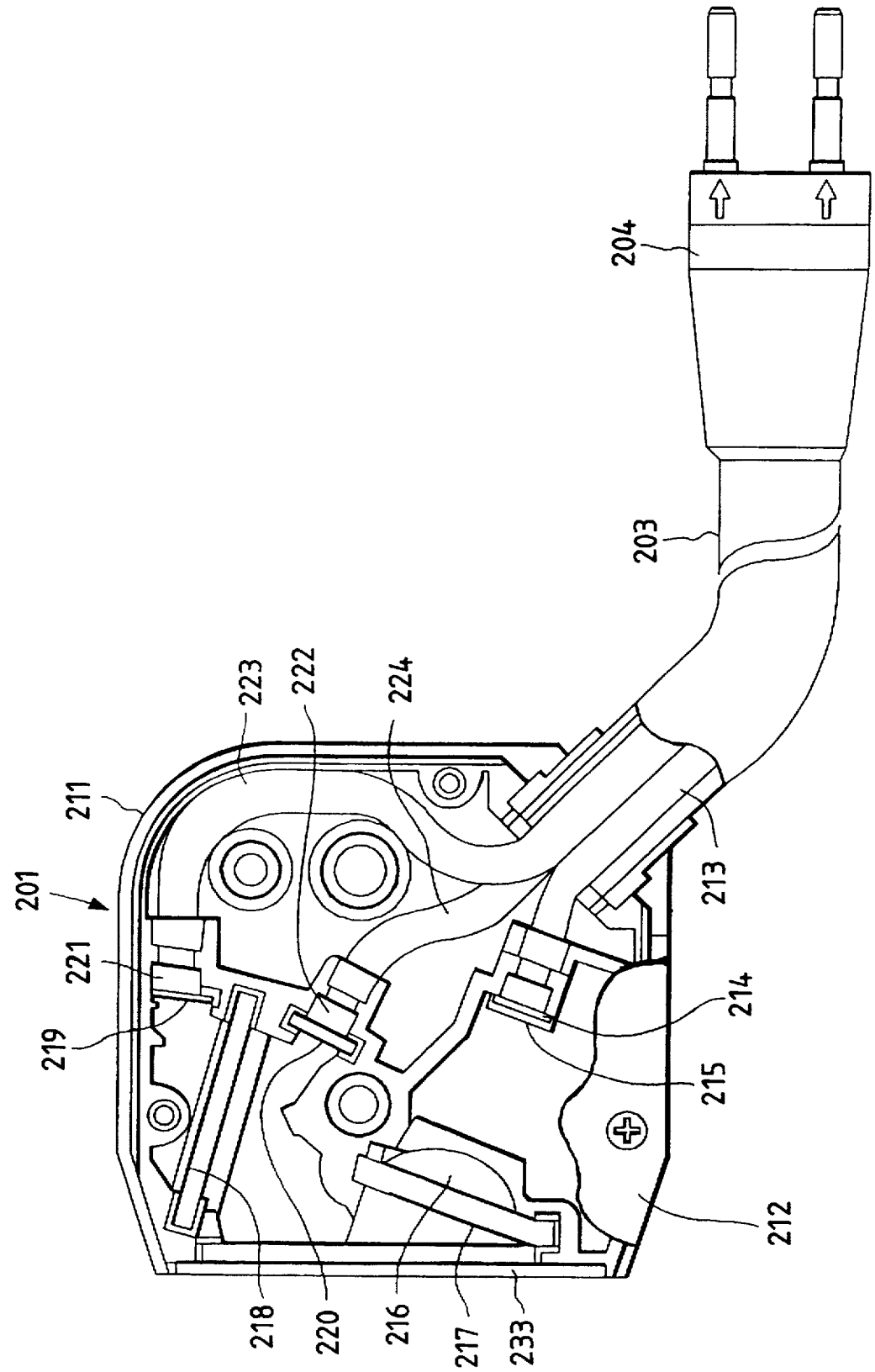

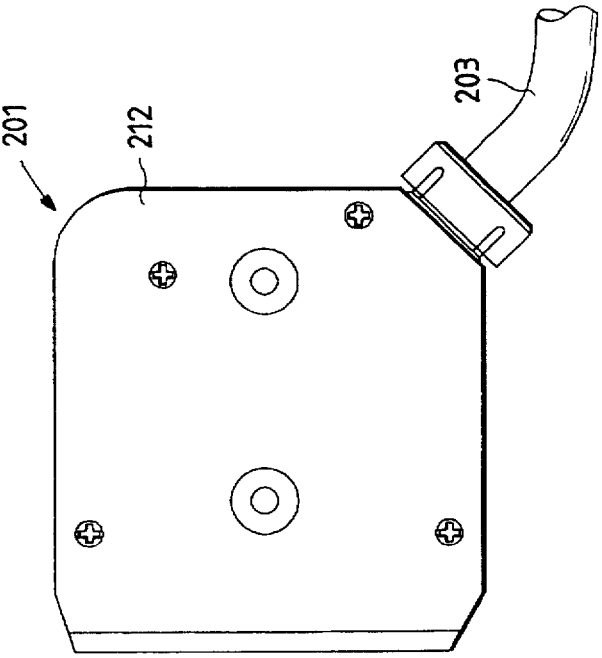
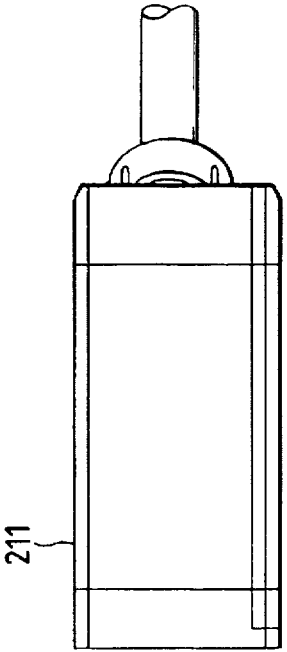
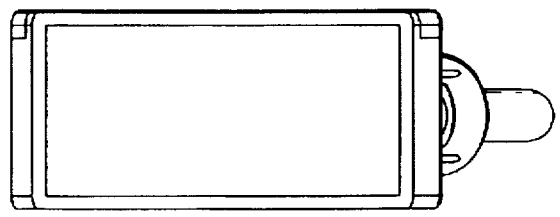

REFLECTION-TYPE PHOTOELECTRIC SENSING APPARATUS

BACKGROUND OF THE INVENTION

1. Field of the Invention

The present invention relates to a reflection-type photoelectric sensing apparatus and, more specifically, to a reflection-type photoelectric sensing apparatus for detecting the existence of an object and its surface state.

2. Description of the Related Art

A reflection-type photoelectric sensing apparatus is known which is constituted of a sensor head unit and an amplifier unit. An illuminating light-emitting element such as a LED, a line sensor, illuminating and receiving lenses, illuminating and photodetecting circuits, and other elements are provided in the sensor head unit. This apparatus detects glossiness or the like of an object by detecting reflection light from an object with the line sensor to obtain its intensity distribution (positional information) and determining a light quantity difference.

However, since many optical elements and circuits are incorporated in the sensor head unit, this conventional sensing apparatus is large, as well as costly because a cumbersome assembling operation is needed. Further, although waterproofness is required in certain environments, the conventional apparatus is insufficient in this respect.

An example of a conventional glossiness detection sensor is disclosed in Japanese Unexamined Patent Publication No. Hei. 4-369468. In this apparatus, light emitted from a light-emitting section is applied to the detection area of an object, and resulting reflection light is detected by a CCD. An output signal of the CCD is differentiated, shaped, and processed for discrimination by use of a given threshold. This apparatus allows detection of an object having high glossiness. However, this apparatus is deficient in being incapable of discriminating between objects having approximately the same glossiness and different reflection light quantities.

SUMMARY OF THE INVENTION

An object of the present invention is to enable positive discrimination between objects that are different in glossiness or reflection light quantity.

Another object of the invention is to provide a reflection-type photoelectric sensing apparatus in which an illuminating light emitting element is removed from a sensor head unit by using illuminating and photodetecting optical fibers, and the positioning and the angle determination of respective optical elements in the sensor head unit can be performed more easily and correctly. Further, it is intended to save space of the sensor head unit, facilitate its assembling, reduce cost and size, and enable stable detection of an object.

A further object of the invention is to improve waterproofness of the sensor head unit.

According to the invention, there is provided a photoelectric sensing apparatus comprising:

illuminating means for applying illumination light to a detection area of a detection sample object or a nondetection sample object, or an actual object;

first and second photodetecting means for detecting first and second reflection light beams reflected from the sample object or the actual object;

glossiness judging means for judging a glossiness of the sample object or the actual object based on outputs of the first and second photodetecting means;

light quantity judging means for judging a light quantity of the sample object or the actual object based on the outputs of the first and second photodetecting means;

evaluation function determining means for determining an evaluation function having at least one of a glossiness and a light quantity as a variable by calculating a glossiness difference and a light quantity difference of the detection sample object and the non-detection sample object;

threshold calculating means for calculating a threshold based on values of the evaluation function of the detection sample object and the non-detection sample object; and object discriminating means for judging whether or not the actual object is an object to be detected by comparing a value of the evaluation function of the actual object with the threshold.

According to another aspect of the invention, there is provided a photoelectric sensing apparatus in which a detection area of an object is illuminated with linearly polarized light, reflection light reflected from the object is separated into two polarization components whose polarization directions are parallel with and perpendicular to a polarization direction of the linearly polarized light by polarized light separating means, and a signal indicating existence, a surface state, or a material of the object is produced based on respective detection outputs of the two polarization components, said apparatus comprising:

an amplifier unit comprising a light-emitting element, photodetecting elements, and a signal processing circuit;

an illuminating optical fiber for guiding light emitted from the light-emitting element to a head unit;

photodetecting optical fibers for guiding the two separated polarization components received by the head unit to the photodetecting elements; and the head unit having a single case accommodating an end portion of the illuminating optical fiber, a polarizing element for producing the linearly polarized light from illumination light output from the illuminating optical fiber, the polarized light separating means, and end portions of the photodetecting optical fibers.

BRIEF DESCRIPTION OF THE DRAWINGS

FIGS. 6A and 6B show photodetection values and glossiness and light quantity values of actual works;

FIG. 7 shows an appearance of an photoelectric sensing apparatus according to a second embodiment of the invention;

FIG. 8 is a partially cutaway view of a sensor head unit of the apparatus of FIG. 7;

FIG. 19 is a vertical sectional view showing a reflection-type photoelectric sensing apparatus according to a third embodiment of the invention;

FIGS. 21A, 21B and 21C are a front view, a side view, and a top view, respectively, of a head unit of the photoelectric sensing apparatus of FIG. 19;

DESCRIPTION OF THE PREFERRED EMBODIMENTS

Embodiment 1

Figure 1:
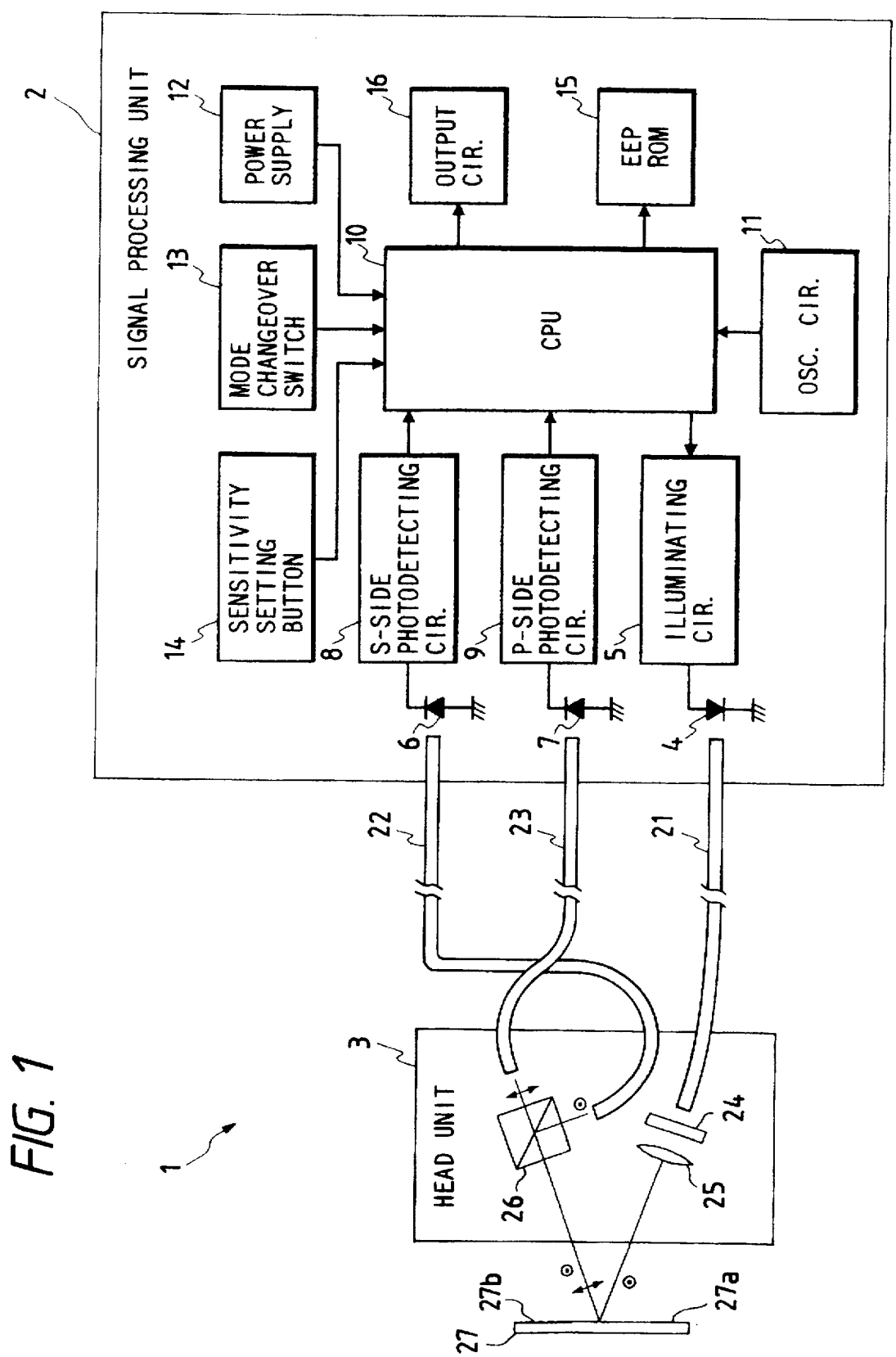
FIG. 1 is a block diagram showing the entire configuration of a photoelectric sensing apparatus according to a first embodiment of the present invention.

FIG. 1 is a block diagram showing the entire configuration of a photoelectric sensing apparatus according to a first embodiment of the invention. As shown in FIG. 1, a photoelectric sensing apparatus 1 is composed of a signal processing unit 2 and a head unit 3. The signal processing unit 2 includes an illuminating circuit 5 for driving an illuminating element 4 at given intervals and S-side and P-side photodetecting circuits 8 and 9 connected to photodetecting elements 6 and 7, respectively. The photodetecting circuits 8 and 9 receive light beams of S-polarization and P-polarization components, respectively, and their outputs are supplied to a microcomputer (CPU) 10. An oscillation circuit 11, a power supply 12, a mode changeover switch 13, a sensitivity setting button 14, an EEPROM (memory), 15, and an output circuit 15 are connected to the microcomputer 10. As described later, the microcomputer 10 drives the illuminating element 5 periodically at a given timing based on inputs from the above components, and detects variations in the surface state of an object by setting thresholds based on photodetection signals.

The configuration of the head unit 3 will be described below. The signal processing unit 2 and the head unit 3 are connected through three optical fibers 21–23. Connected at one end to the illuminating element 4, the optical fiber 21 serves as an illumination optical fiber. A lens 25 is disposed adjacent to the head-side end of the optical fiber 21 with a filter 24 interposed in between. The filter 24 is a polarizing filter that outputs only an S-polarization component. A polarizing beam splitter 26 is disposed at a position of receiving reflection light of the above illumination light. The polarizing beam splitter 26 separates received light into an S-polarization component and a P-polarization component, which enter photodetecting optical fibers 22 and 23, respectively. The other ends of the photodetecting optical fibers 22 and 23 are connected to the photodetecting elements 6 and 7 of the signal processing unit 2, respectively.

The mode changeover switch 13 serves to switch between a run mode and a teach mode. In the teach mode, every time the sensitivity setting button is depressed, outputs of the photodetecting circuits 8 and 9 which are produced in response to detection signals of the photodetecting elements 6 and 7 are A/D-converted and input to the microcomputer 10. Based on the received values, the microcomputer 10 sets coefficients of an evaluation function and detection and non-detection levels. In the run mode, current signal levels are compared with the detection and non-detection levels thus set, and an on/off signal is produced.

The operation of this embodiment will be hereinafter described with reference to a flowchart of FIGS. 2 and 3. Upon start of a process, it is checked at step 31 whether the mode changeover switch 13 is on the teach-mode side. If a judgment result is affirmative, the process goes to step 32, where it is checked whether the sensitivity setting button 14 has been depressed. The process waits for depression of the button 14. In setting sensitivity, a work 27 is disposed in front of the head unit 3 as shown in FIG. 1. The work 27 has a white field area 27a that should not be detected and a tape area 27b in which a transparent tape is stuck to, the white field. These two areas 27a and 27b are to be discriminated from each other.

First, the sensitivity setting button 14 is depressed after an arrangement is so made as to allow the white field area 27a of the work 27 to be illuminated with light emitted from the illuminating element 4. Then, at step 33, the illuminating element 4 is driven through the illuminating circuit 5. As a result, light is input to the polarizing filter 24 via the optical fiber 21, and only an S-polarization component is applied to the white field area 27a of the work 27 from the polarizing filter 24. Resulting reflection light is separated by the polarizing beam splitter 26 into S-polarization and P-polarization components, which are supplied to the photodetecting elements 6 and 7 of the signal processing unit 2 via the optical fibers 22 and 23 and detected thereby. Resulting detection signals are converted into voltage signals by the S-side and P-side photodetecting circuits 8 and 9, respectively, and then A/D-converted in the microcomputer 10. At step 34, the microcomputer 10 takes in the voltage signals of the S-polarization and P-polarization components as $S_A$ and $P_A$, respectively. After the work 27 is so moved that its tape area 27b is illuminated, the sensitivity button 14 is again depressed at step 35. As a result, the illuminating circuit 5 is driven in the same manner as in the above, and only an S-polarization component of light coming from the illuminating element 4 via the illumination optical fiber 21 is extracted by the filter 24 and applied to the tape area 27b (area B) of the work 27. Resulting reflection light is separated by the polarizing beam splitter 26 into S-polarization and P-polarization components, and the microcomputer 10 takes in corresponding A/D-converted voltage signals $S_B$ and $P_B$ (step 37). At step 38, a glossiness X is judged from a difference between the voltages corresponding to the S-polarization and P-polarization components in a manner described later. At step 39, a light quantity Y is judged from a sum of those voltages. At step 40, coefficients a and b for defining an evaluation function Z are determined by using the glossiness X and the light quantity Y. At step 41, a detection level $Th_{on}$ and a non-detection level $Th_{off}$ are set. At step 42, the detection level $Th_{on}$ and the non-detection level $Th_{off}$ and the coefficients a and b are written to the EEPROM 15. Thus, the teach-mode process is completed.

Figure 4A:
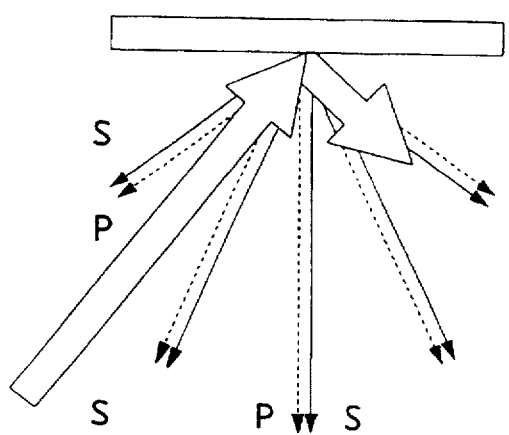
FIG. 4A schematically illustrates a relationship between specular reflection light and diffuse-reflection light in a case where S-polarization light is incident on an object having a small glossiness.
Figure 4B:
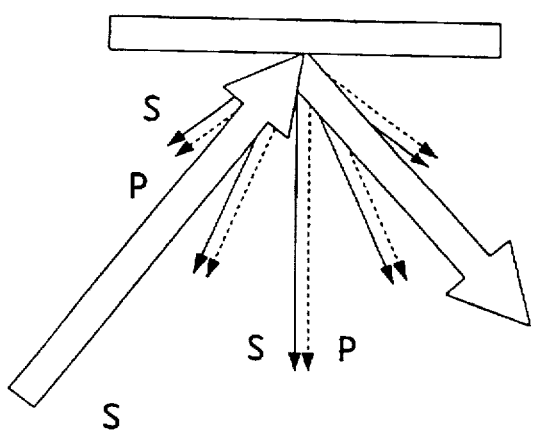
FIG. 4B schematically illustrates a relationship between specular reflection light and diffuse-reflection light in a case where S-polarization light is incident on an object having a large glossiness.

Next, a description will be made of the setting of the coefficients a and b and the detection and non-detection levels $Th_{on}$ and $Th_{off}$. FIGS. 4A and 4B schematically illustrate how incident light is reflected by objects having small and large glossiness values, respectively. As shown in FIG. 4A, when incident light of one of the two types of polarization, say, S-polarization, strikes an object having a small glossiness, there is produced polarization-direction-preserved specular reflection light as well as high-intensity diffuse-reflection light in which S-polarization and P-polarization components have the same level. On the other hand, as shown in FIG. 4B, in the case of an object having a large glossiness, there are produced low-intensity diffuse-reflection light in which S-polarization and P-polarization components have the same level and polarization-direction-preserved, i.e., S-polarization specular reflection light of a relatively low level. Therefore, the glossiness can be determined from a difference between the S-polarization and P-polarization components.

In this embodiment, the work 27 has the surface 27a having a small glossiness and the surface 27b having a large glossiness, and these surfaces are discriminated from each other. However, in general, an object A to be detected and an object B not to be detected are illuminated, and coefficients and thresholds are set to discriminate between the objects A and B. Voltages of S-polarization and P-polarization components produced from the work surface A are denoted by $S_A$ and $P_A$, respectively, and voltages of S-polarization and P-polarization components produced from the work surface B are denoted by $S_B$ and $P_B$, respectively. With this notation, glossiness values $X_A$ and $X_B$ and light quantities $Y_A$ and $Y_B$ are defined as follows:

$$X_A = S_A - P_A$$

$$X_B = S_B - P_B$$

$$Y_A = S_A + P_A$$

$$Y_B = S_B + P_B$$

Further, a glossiness difference $X_S$ and a light quantity difference $Y_S$ between the work surfaces A and B are defined as follows:

$$X_S = \frac{|X_A - X_B|}{X_A + X_B} \times 100$$

$$Y_S = \frac{|Y_A - Y_B|}{Y_A + Y_B} \times 100$$

With this definition, each of $X_S$ and $Y_S$ varies in a range of 0 to 100. An evaluation function Z is defined as follows for a glossiness X and a light quantity Y:

$$Z = aX + bY$$

where coefficients a and b are defined from the glossiness difference $X_S$ and the light quantity difference $Y_S$ as follows:

$$a = 10 - b$$

$$b = Y_S - X_S^2 j$$

where b has a minimum value of 0 and a maximum value of 10, as hereinafter described.

Values of the evaluation function Z which are obtained when the work surfaces A and B are illuminated are denoted by $Z_A$ and $Z_B$, respectively. Further, thresholds $Th_{on}$ and $Th_{off}$ to be used for detecting an object to be detected are defined as follows:

$$Th_{on} = \frac{Z_A + Z_B}{2} + 20$$

$$Th_{off} = \frac{Z_A + Z_B}{2} - 20$$

Figure 5:
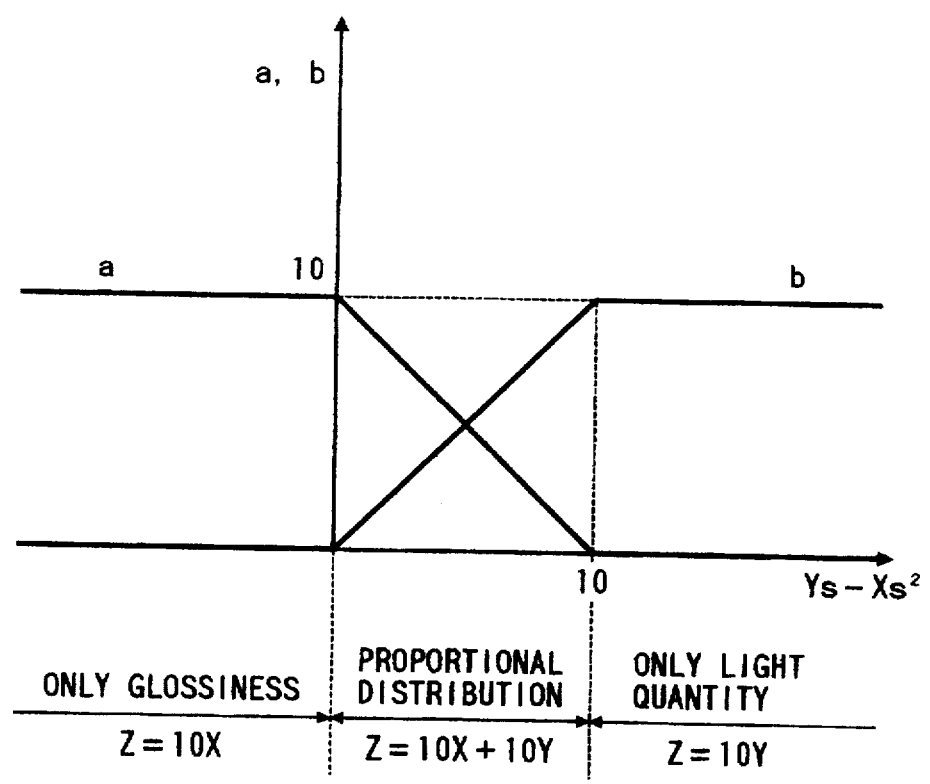
FIG. 5 is a graph showing an evaluation function.

FIG. 5 is a graph showing a relationship between $Y_S - X_S^2$ and the coefficients a and b. For a range of $Y_S - X_S^2$ larger than 10, b has a constant value 10. For a range of $Y_S - X_S^2$ smaller than 0, b is fixed at 0. Where $Y_S - X_S^2$ is between 0 and 10, b is equal to $Y_S - X_S^2$ and varies continuously. Thus, the sum of a and b is always equal to 10. This technique is intended to select between discrimination based on either the glossiness or light quantity and discrimination based on both glossiness and light quantity (proportional distribution). As shown in FIG. 5, when b is 10, a is equal to 0 and therefore the evaluation function Z is expressed as Z=10Y, that is, determined only by the light quantity Y. When b is 0, a is equal to 10 and therefore the evaluation function Z is expressed as Z=10X, that is, determined only by the glossiness X. Between these two ranges, the evaluation function Z is expressed as Z=aX+bY, that is, determined by proportional distribution of the glossiness X and the light quantity Y. In this case, b is equal to $Y_{S-XS}^2$.

Next, a description will be made of an example of calculation in detecting, that is, discriminating between objects having large and small glossiness values. Referring to FIG. 6A, a tape is stuck to a white drawing sheet in area B and the other area of the drawing sheet is referred to as area A. The white field area A of the white drawing sheet has a small glossiness and the tape area B has a large glossiness. For example, A/D-converted values of S-polarization and P-polarization components obtained by reflection at the white field area A are assumed to be 70 and 50, respectively, and A/D-converted values of S-polarization and P-polarization components obtained by reflection at the tape area B are assumed to be 160 and 50, respectively. In this case, $X_A$ and $X_B$ are respectively equal to 20 and 110, and $Y_A$ and $Y_B$ are respectively equal to 120 and 210, respectively. Therefore, the glossiness difference $X_S$ and the light quantity difference $Y_S$ are calculated as 69 and 27, respectively. The coefficients a and b are calculated as $$b = Y_S - X_S^2 = -4,734 \rightarrow 0$$

$$a = 10 - b = 0.$$

Therefore, the evaluation function Z is $$Z = 10x.$$

Once the evaluation function Z is determined in the above manner, an evaluation function value $Z_A$ of the white field area A and an evaluation function $Z_B$ of the tape area B are calculated as $$Z_A = 10X_A = 200$$

$$Z_B = 10X_B = 1,100.$$

The thresholds $Th_{on}$ and $Th_{off}$ are determined as follows:

$$Th_{on} = (Z_A + Z_B)/2 + 20 = 670$$

$$Th_{off} = (Z_A + Z_B)/2 - 20 = 630$$

These thresholds allow the output signal to have an on state for an area having a large glossiness (tape area B) and an off state for an area having a small glossiness (white field area A of a white drawing sheet).

A description will be made of another example of calculation in detecting, that is, discriminating between objects having approximately the same glossiness and different colors. Referring to FIG. 6B, work A is made of white, glossy plastics and work B is made of black, glossy plastics, both having large glossiness values. A/D-converted values $S_A$ and $P_A$ of S-polarization and P-polarization components obtained by reflection at work A are assumed to be 160 and 50, respectively, and A/D-converted values of S-polarization and P-polarization components obtained by reflection at work B are assumed to be 110 and 2, respectively. The glossiness X and the light quantity Y have values shown in FIG. 6B, and the glossiness difference $X_S$ and the light quantity difference $Y_S$ are calculated as 1 and 30, respectively. In this case, the coefficients a and b of the evaluation function Z are determined as follows:

$$b=Y_S-X_S^2=29-10$$

$$a=10-b=0$$

Therefore, the evaluation function Z is
$Z=10Y$.
Evaluation function values $Z_A$ and $Z_B$ are
$Z_A=2,100$
$Z_B=1,120$.
Detection and non-detection levels $Th_{on}$ and $Th_{off}$ are calculated as
$Th_{on}=1,630$
$Th_{off}=1,590$.
These thresholds allow the output signal to have an on state for object A made of white, glossy plastics and an off state for object B made of black, glossy plastics, to enable discrimination between them.

In the above process, the microcomputer 10 serves as a glossiness judging means for judging glossiness based on outputs of first and second photodetecting means at step 38, and a light quantity judging means for judging a reflection light quantity based on the same outputs at step 39. The microcomputer 10 also constitutes an evaluation function determining means for determining, based on a glossiness difference and a light quantity difference of an object to be detected and an object not to be detected, an evaluation function Z in which at least one of the glossiness and the light quantity is a variable at step 40, and a threshold calculating means for calculating thresholds based on values of the evaluation function at step 41.

Figure 2:
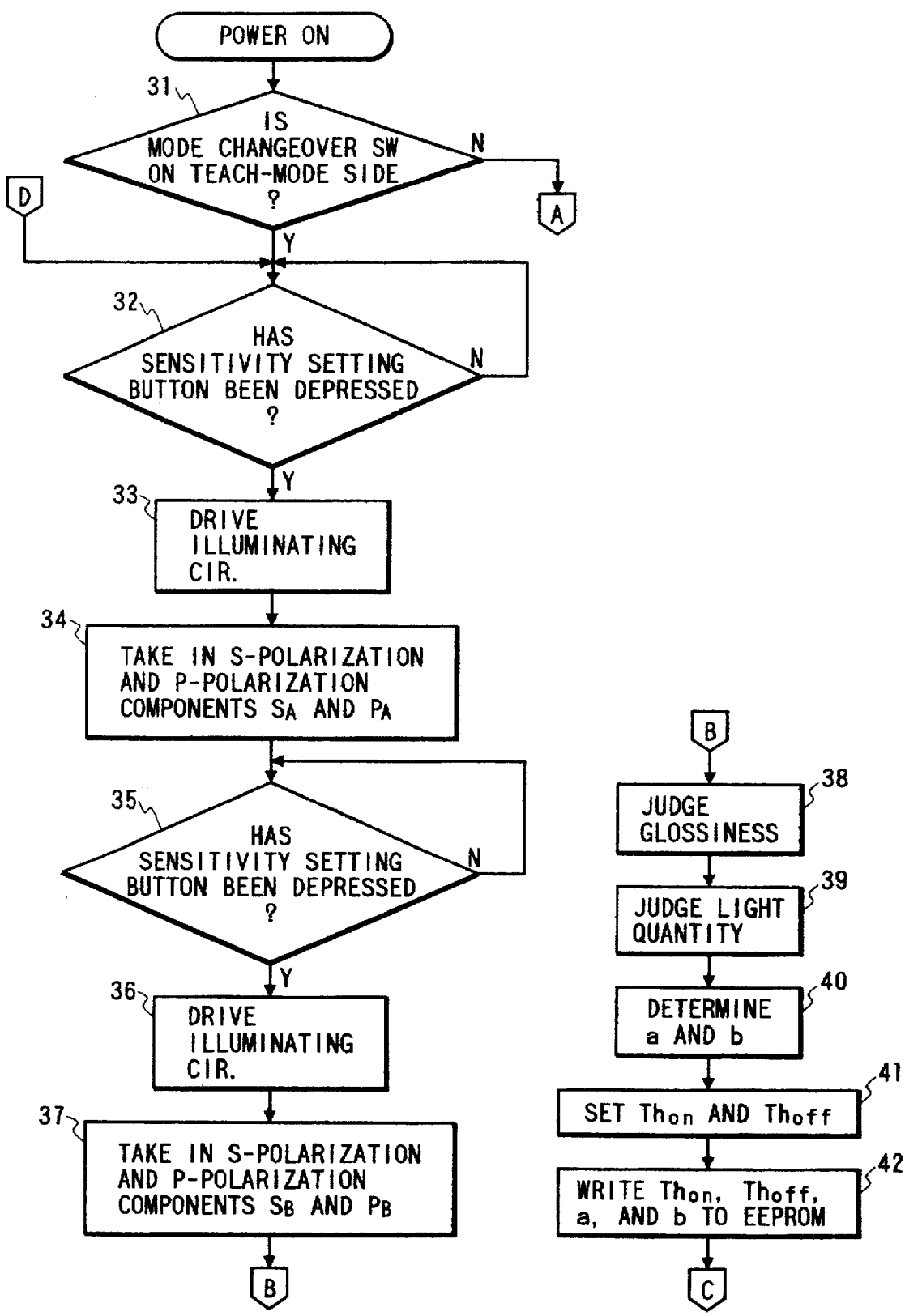
FIGS. 2 and 3 are a flowchart showing the operation of the photoelectric sensing apparatus according to the first embodiment.
Figure 3:
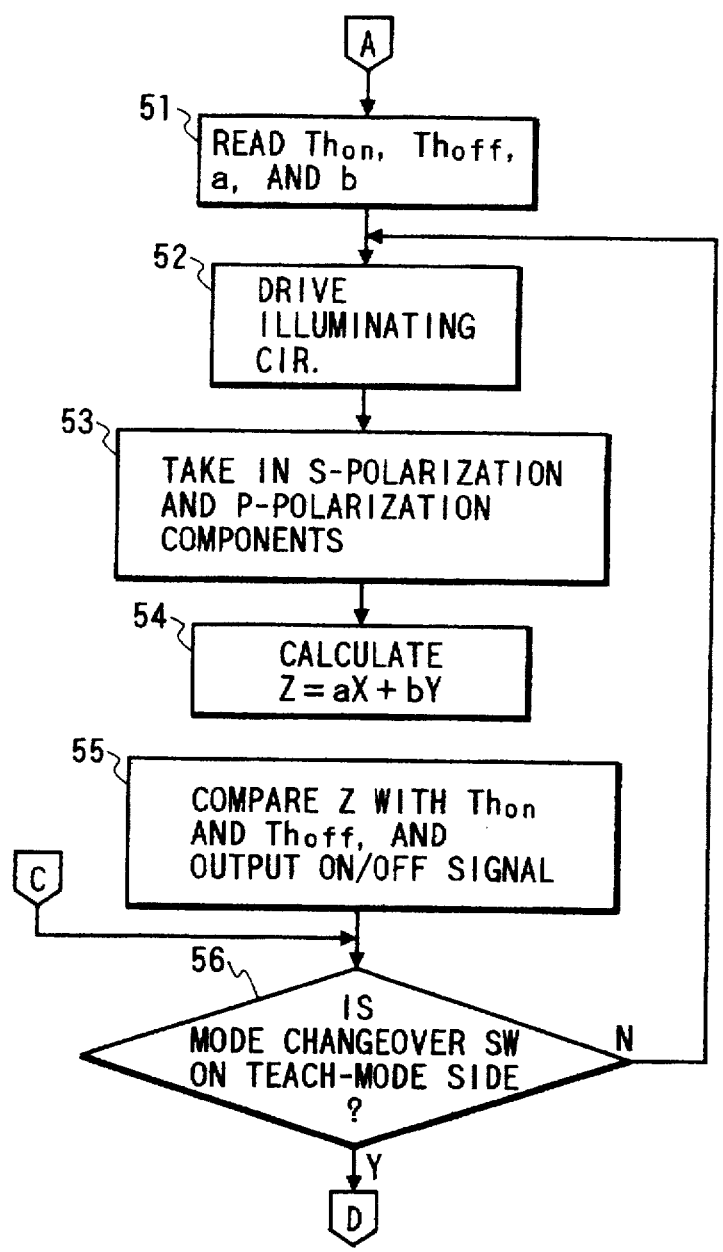

Referring to the flowchart of FIGS. 2 and 3, if the mode changeover switch 13 is on the run-mode side in the judgment of step 31, the process goes to step 51 (FIG. 3), where the detection level $Th_{on}$ and the non-detection level $Th_{off}$ and the coefficients a and b are read out from the EEPROM 15. At step 52, the illuminating circuit 5 is driven. As a result, light is emitted from the illuminating element 4, sent via the optical fiber 21, only an S-polarization component is applied to a work from the polarizing filter 24. Resulting reflection light is separated into S-polarization light and P-polarization light, which are received by the photodetecting elements 6 and 7. The microcomputer 10 takes in A/D-converted values of outputs of the photodetecting elements 6 and 7 at step 53. At step 54, A value of the evaluation function Z are calculated according to $$Z=aX+bY.$$

At step 55, the calculated value of Z is compared with the detection level $Th_{on}$ and $Th_{off}$ and an on/off signal is output.

At step 56, it is checked whether the mode changeover switch 13 is on the teach-mode side. If it is not on the teach-mode side, the process returns to step 52 to repeat the above operation. Conversely, if the mode changeover switch 13 is on the teach-mode side at step 56, the process returns to step 32 (FIG. 2) to execute steps 33-42, to thereby set coefficients a and b and detection and non-detection levels $Th_{on}$ and $Th_{off}$.

In the above manner, two kinds of objects can be discriminated from each other by using the thresholds and the evaluation function thus set. The microcomputer 10 serves as an object discriminating means for discriminating between an object to be detected and an object not to be detected by comparing, with the thresholds, an evaluation function value that is calculated from outputs of the glossiness judging means and the light quantity judging means.

Although in this embodiment only S-polarization light is applied to an object from the illuminating means and resulting reflection light beams are detected, it goes without saying that object discrimination can be performed by applying P-polarization light to an object, detecting resulting reflection light beams, and performing operations similar to the above.

Although in the above embodiment an evaluation function is automatically determined from a glossiness difference and a light quantity difference, it may be determined based on a proportion between the glossiness and the light quantity which proportion is input to the microcomputer 10 from a proportion input means in the form of a voltage set by a variable resistor, for instance.

In the above embodiment, a glossiness and a light quantity are determined by applying linearly polarized light to an object and detecting orthogonally polarized reflection light beams by the two photodetecting means. A modification is possible in which a glossiness is determined by the conventional technique described in the background section, a light quantity is determined from a sum of outputs of a CCD, and an object is detected by the glossiness and the light quantity thus determined.

As described above, according to the invention, a teaching operation for a plurality of objects that are different in at least one of glossiness and light quantity is preliminarily performed to set an evaluation function and thresholds. Discrimination between objects can be performed positively based on the evaluation function and the threshold thus determined.

Embodiment 2

FIG. 7 shows an appearance of a photoelectric sensing apparatus according to this embodiment. A photoelectric sensing apparatus 100 consists of a sensor head unit 101, an amplifier unit 102, and an optical fiber cable 123 and a connector 124 for connecting the units 101 and 102. The sensor head unit 101 has an illuminating section for illuminating an object 104 to be detected, and a light receiving section for receiving resulting reflection light. The amplifier unit 102 has a light emitting section for emitting light to be supplied to the illuminating section, circuits for judging the existence of the object 104 and its surface state such as glossiness, and other components.

Figure 9A:
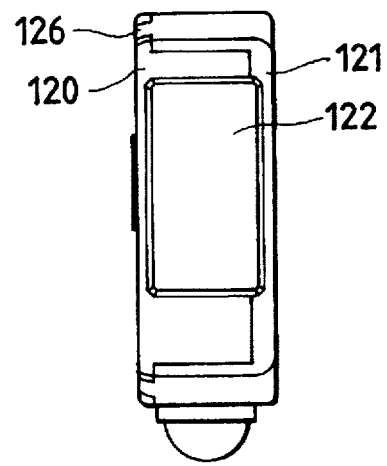
FIGS. 9A and 9B are front and top view of the sensor head unit of FIG. 8.
Figure 9B:
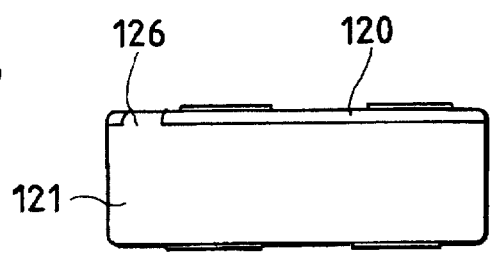
Figure 10:
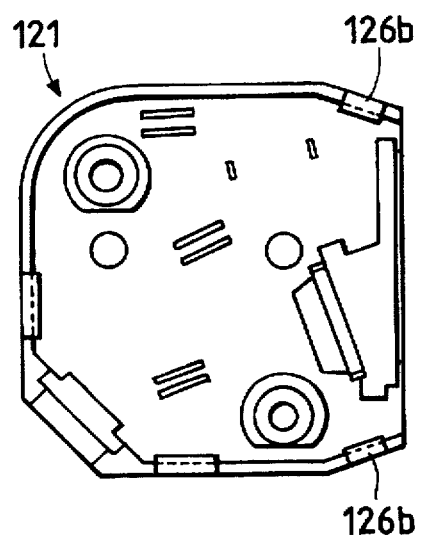
FIG. 10 is a side view showing the inside of a cover body of the sensor head unit of FIG. 8.
Figure 11:
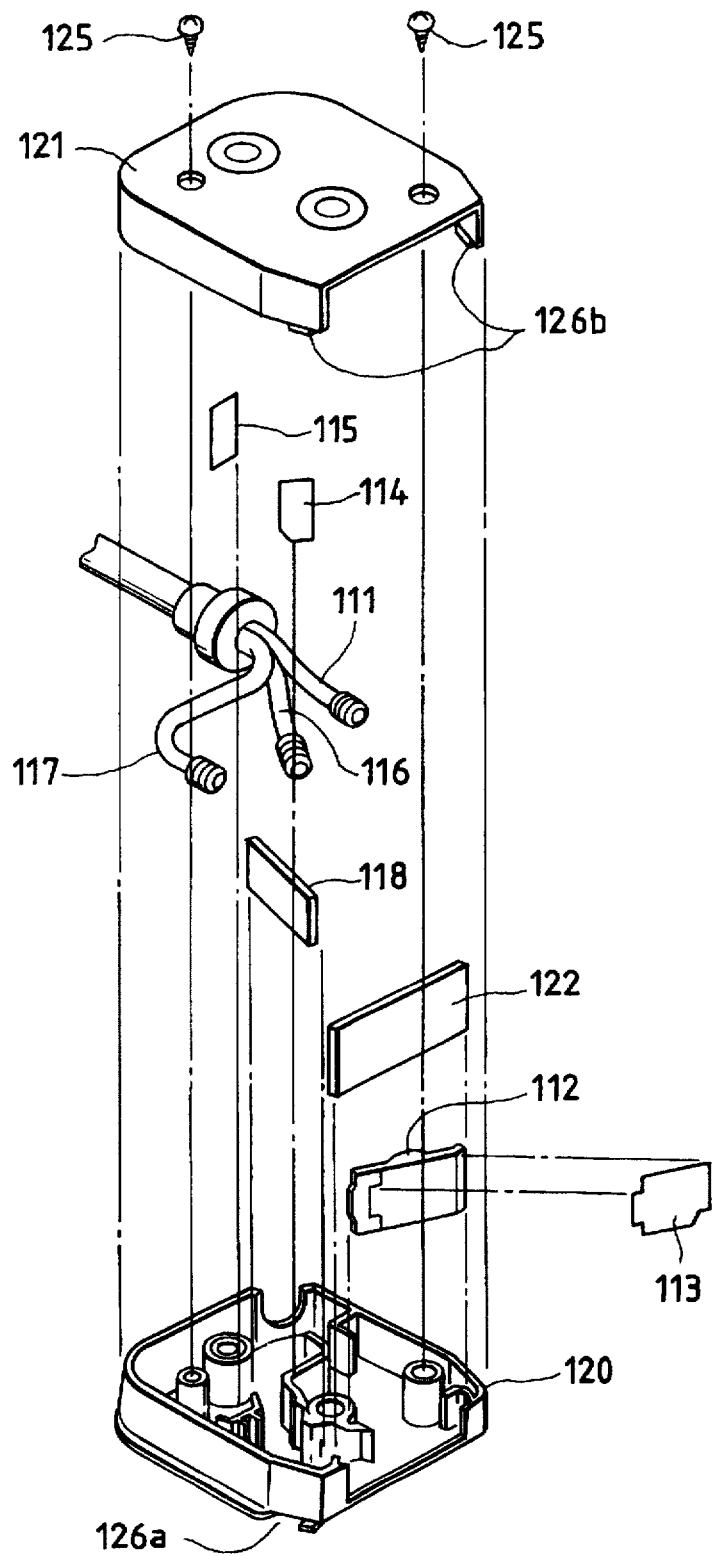
FIG. 11 is an exploded view of the sensor head unit of FIG. 8.

FIG. 8 is a partially cutaway view showing a detailed configuration of the sensor head unit 101. FIGS. 9A and 9B are a front view and a top view of the sensor head unit 101. FIG. 10 a side view showing the inside of a cover body 121 of the sensor head unit 101. FIG. 11 is an exploded view of the sensor head unit 101. As seen from these figures, the outer structure of the sensor head unit 101 is composed of a base body 120 and the cover body 121 that are fitted together. Various optical elements incorporated in the sensor head unit 101 are mainly fixed to the base body 120 at given positions, and the cover body 121 is so mounted as to cover the optical elements. As for the internal structure of the sensor head unit 101, the illuminating section is composed of an illuminating fiber 111, an illuminating lens 112, and a polarizing filter 112, and the light receiving section is constituted of polarizing filters 114 and 115 and photodetecting fibers 116 and 117. A polarizing beam splitter 118 is disposed between the object 104 and the light receiving section. The polarizing beam splitter 118 separates reflection light coming from the object 104 into a light beam mainly composed of an S-polarization component and a light beam mainly composed of a P-polarization component. End faces of the photodetecting optical fibers 116 and 117 are inclined from the optical axes by a given angle.

The above optical elements are held by the base body 120, and the cover body 121 is fitted to the opening side of the base body 120. Thus, the optical elements are fixed being interposed between the bodies 120 and 121. A transparent window glass 122 for preventing invasion of dust is provided on the front side for the illumination and light reception. Each of the illuminating fiber 111 and the photodetecting fibers 116 and 117 is a bundle fiber, and they are curved in a desired manner by means of fiber guide members that are integral with the base body 120. Thus, the fibers 111, 116 and 117 are accommodated in a saved space, enabling size reduction of the sensor head unit 101. The three fibers are bundled into a fiber cable 123 by use of a tube so as to be movable relative to each other. The other ends of the fibers are connected to the connector 124 (in FIG. 8, two fibers are superimposed one on another), and coupled to a light-emitting element and photodetecting elements that are incorporated in the amplifier unit 102.

Flange portions including inclined faces (in a side view) of the base body 120 and the cover body 121 are respectively formed with cuts 126a and protrusions 126b (snap fits 126) that are fitted together in an assembled state. With this structure, there occurs no play between the base body 120 and the cover body 121: they are fixed to each other without any lateral deviation. Further, this structure allows the sensor head unit 101 to be assembled easily in a smaller number of steps. The base body 120 and the cover body 121 are assembled and disassembled by use of tapping screws 125. As shown in FIGS. 8 and 11, mainly the base body 120 is integrally formed with light shielding members 127, 128, etc. for reducing stray light along the illuminating and light reception paths. The light shielding member 128 also serves as one screw hole 129 for assembling of the sensor head unit 101. The other screw hole 30 also serves as a member for guiding the optical fibers 116 and 117. With this structure, the optical fibers 116 and 117 can be bent at small radii, enabling size reduction of the sensor head unit 101. There can be avoided a cost increase due to needless members. In addition, stray light can be reduced in a positive manner.

The operation of the above-constructed photoelectric sensing apparatus 100 will be described below. Light emitted from the illuminating fiber 111 are focused on the object 104 by the illuminating lens 112. In this case, only S-polarization light is transmitted from the polarizing filter 113 and applied to the incident surface of the object 104. S-polarization light of reflection light from the object 104 is reflected by the polarizing beam splitter 118 and input to the photodetecting fiber 116, and its P-polarization light is transmitted to enter the photodetecting fiber 117. Since the polarization direction of a specular reflection component of the reflection light from the object 104 is preserved (S-polarization is maintained), all of the specular reflection component is input to the photodetecting fiber 116. On the other hand, having random polarization directions, diffuse-reflection components are distributed to the photodetecting fibers 116 and 117 approximately equally. Therefore, a specular reflection light quantity, that is, glossiness of the object 104 can be detected by calculating a difference between reception light quantities of the photodetecting fibers 116 and 117.

Since the end face of each of the photodetecting fibers 116 and 117 is inclined from the optical axis by a given angle (for instance, about 25°), a variation of the reception light quantity caused by a variation in detection distance l (see FIG. 8) is small. For example, for a detection distance range of 10±3 mm, a variation of the reception light quantity of the face-inclined photodetecting fibers 116 and 117 is as small as about ±20% while that of photodetecting fibers 116 and 117 without face inclination is about ±50%. Where fibers are used for the photodetection purpose, a desired effect can be obtained by slightly inclining the fibers because they have superior directivity. Therefore, being insensitive to noise, the apparatus can detect the object 104 in a stable manner.

Figure 12A:
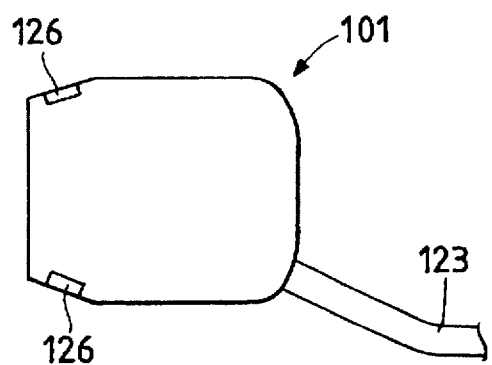
FIGS. 12A and 12B illustrate a difference in operation between a structure of the sensor head unit of the second embodiment and another structure.
Figure 12B:
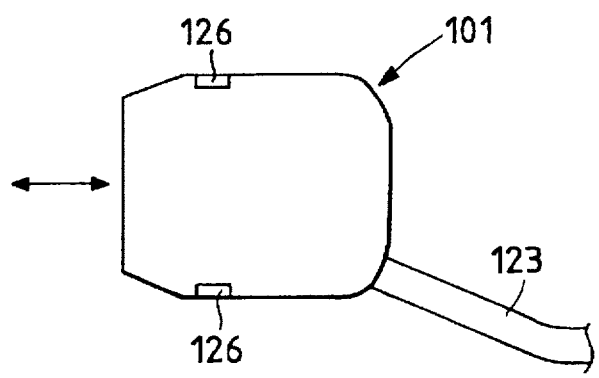

FIGS. 12A and 12B illustrate a difference in operation between a case where the snap fits 26 are provided in the flange portions including the inclined faces of the sensor head unit 101 as in this embodiment (FIG. 12A) and a case where they are provided in flange portions that are not inclined (FIG. 12B). Lateral deviation (indicated by an arrow) is less likely to occur in the structure of FIG. 12A than in the structure of FIG. 12B. Therefore, in the structure of FIG. 12A, the individual optical elements hardly deviate from the optical axis, so that the assembling becomes easier.

Figure 13A:
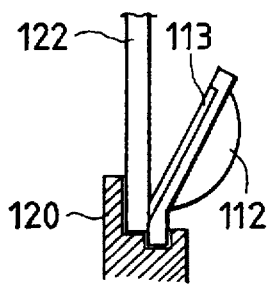
FIGS. 13A and 13B illustrate a difference between a structure for fixing an imaging lens to the base body in the sensor head unit of the second embodiment and another structure.
Figure 13B:
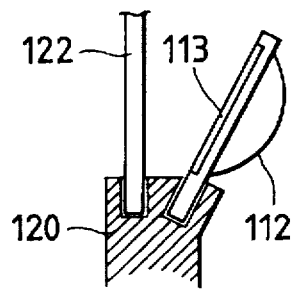

FIG. 13A shows how the illuminating lens 112 and the transparent window glass 122 are fixed to the base body 120 in this embodiment. For comparison, FIG. 13B shows another structure of the same portion. Referring to FIG. 13A, in this embodiment, an end portion of the illuminating lens 112 is bent so that it is fixed to the base body 120 together with the transparent window glass 122. In the structure of FIG. 13B, they are fixed to the base body 122 separately. The sensor head unit 101 can be made smaller with the structure of this embodiment than with the structure of FIG. 13B. The polarizing filter 113 is fixed to the illuminating lens 112 so as to be in close contact with the latter. Since the end portions of the respective optical fibers 111, 116 and 117 are formed with sleeves and the sleeves are pressure-inserted in the base body 120, the sensor head unit 101 can be made smaller, and the positioning between the optical fibers and the other optical elements and the determination of angles therebetween can be performed easily.

Figure 14A:
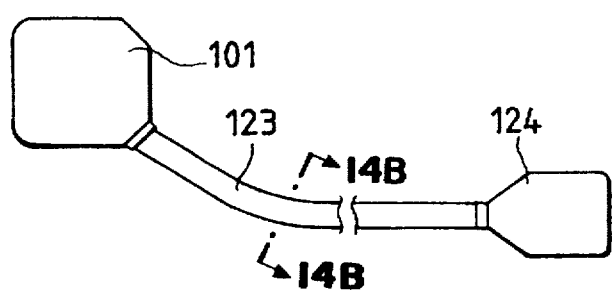
FIGS. 14A and 14B, 15, 16, 17 and FIGS. 18A, 18B and 18C show examples of structures of a fiber cable.
Figure 14B:
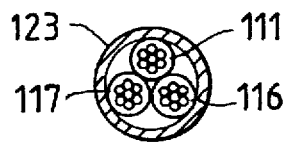
Figure 15:
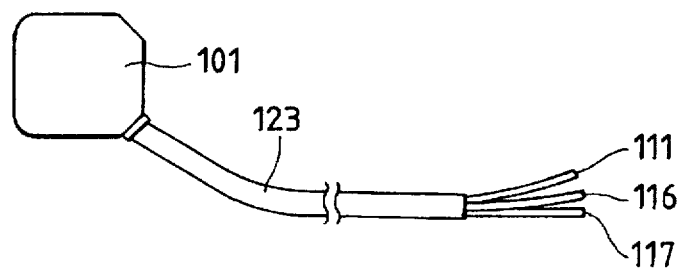
Figure 16:
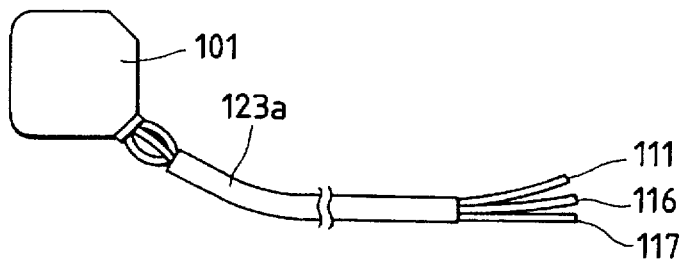
Figure 17:
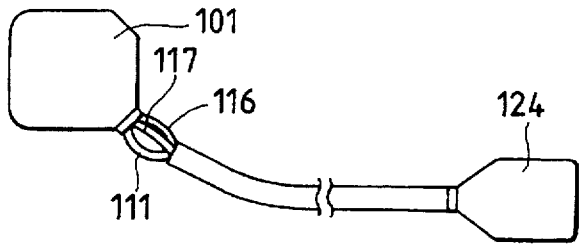
Figure 18A:
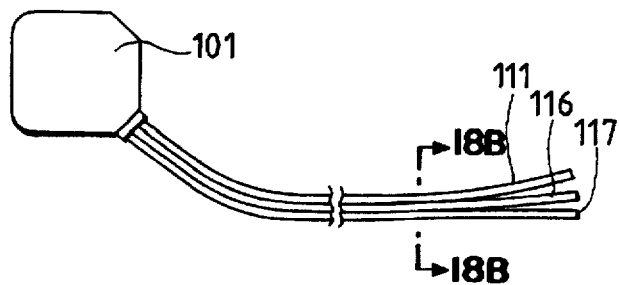
Figure 18B:
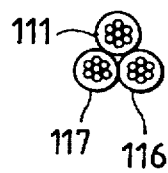
Figure 18C:
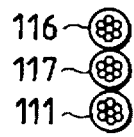

Next, with reference to FIGS. 14A and 14B to FIGS. 18A and 18B, a description will be made of structures of a portion of the fiber cable 123 between the sensor head unit 101 and the connector 124, in each of which structures a plurality of illuminating and photodetecting fibers are bundled together. The structure of FIGS. 14A and 14B is equivalent to that shown in FIG. 8. As shown in FIG. 14B, which is a sectional view taken along line 14B—14B in FIG. 14A, the three fibers 111, 116 and 117 for illumination and light reception are together inserted in a flexible, tube-like jacket 128. In the structure of FIG. 15, the end portions of the fibers 111, 116 and 117 to be connected to the amplifier unit 102 are separated from each other. In the structure of FIG. 16, only an intermediate portion of the three fibers 111, 116 and 117 are covered with a jacket 123a. In the structure of FIG. 17, a connector 124 is added to the structure of FIG. 16. In the structure of FIGS. 18A–18C (FIG. 18B is a sectional view taken along line 18B—18B in FIG. 18A; FIG. 18C is a sectional view of an alternate form), the three fibers 111, 116 and 117 are bonded to each other in triangular form (FIG. 18B) or planar form (FIG. 18C).

The above structures provide the following advantages. In the case of a plurality of illuminating and photodetecting fibers that are not bundled together, when bending or twisting stress, for instance, is applied to one of the photodetecting fibers, a loss occurs in the reception light quantity of that fiber, disabling production of a correct signal processing result. Further, when one of the photodetecting fibers is damaged, an output of the head sensor unit 101 is kept wrong, possible producing an undesirable signal. In contrast, in the above configurations, stress acts on the illuminating and photodetecting fibers evenly in the same phase. Therefore, the stress less affects the signal processing, and the apparatus operates toward a safer side even if a fiber is damaged. Further, since the plurality of fibers are bundled together, the tensile strength and the flexural strength can be improved.

For example, the photoelectric sensing apparatus 100 of this embodiment can be used as a sensor of a testing apparatus (not shown) for checking, based on differences in glossiness, whether label have been stuck to bottles, cases, boxes, or the like by a label sticking apparatus disposed adjacent to a conveyor in manufacture of bottles, or the like. It can also be used as a color mark sensor for checking, based on a packing register mark itself or a difference in color, whether the mark is correctly attached to a product.

As described above, according to the photoelectric sensing apparatus of the invention, the sensor head unit is constructed such that the base body and the cover body in which the optical elements including the illuminating and photodetecting fibers are fixed are secured by means of the snap fit structure so as not to deviate from each other in a lateral direction. Therefore, the positioning and the angle determination of the optical elements can be constructed easily and correctly. Objects can be detected in a stable manner. Further, assembling can be performed easily, and the cost can be reduced. In addition, since no light-emitting element needs to be incorporated in the sensor head unit, space is saved as much, contributing to size reduction of the sensor head unit.

Embodiment 3

Figure 20:
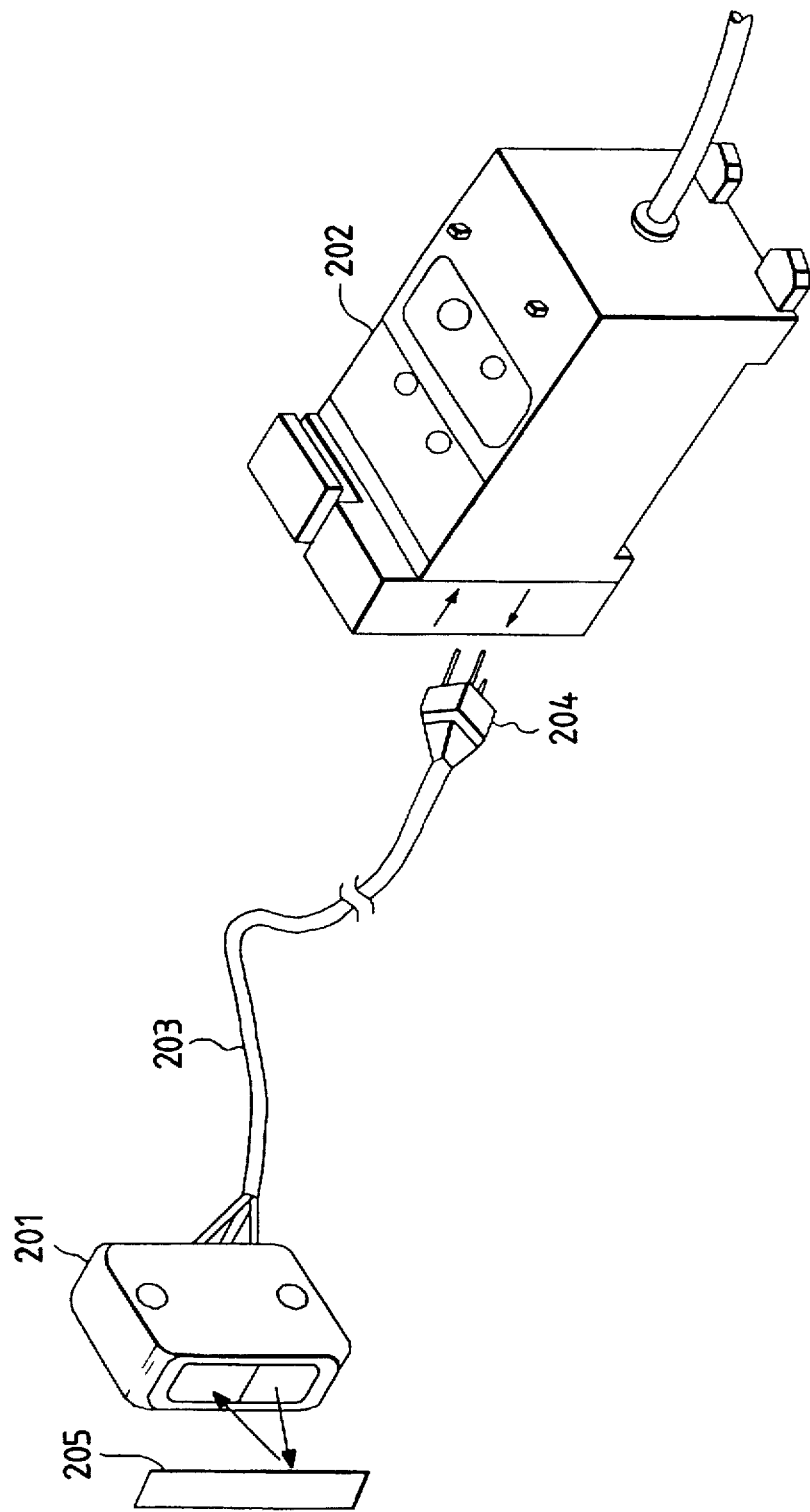
FIG. 20 is a perspective view showing the entire configuration of the reflection-type photoelectric sensing apparatus of FIG. 19.
Figure 22:
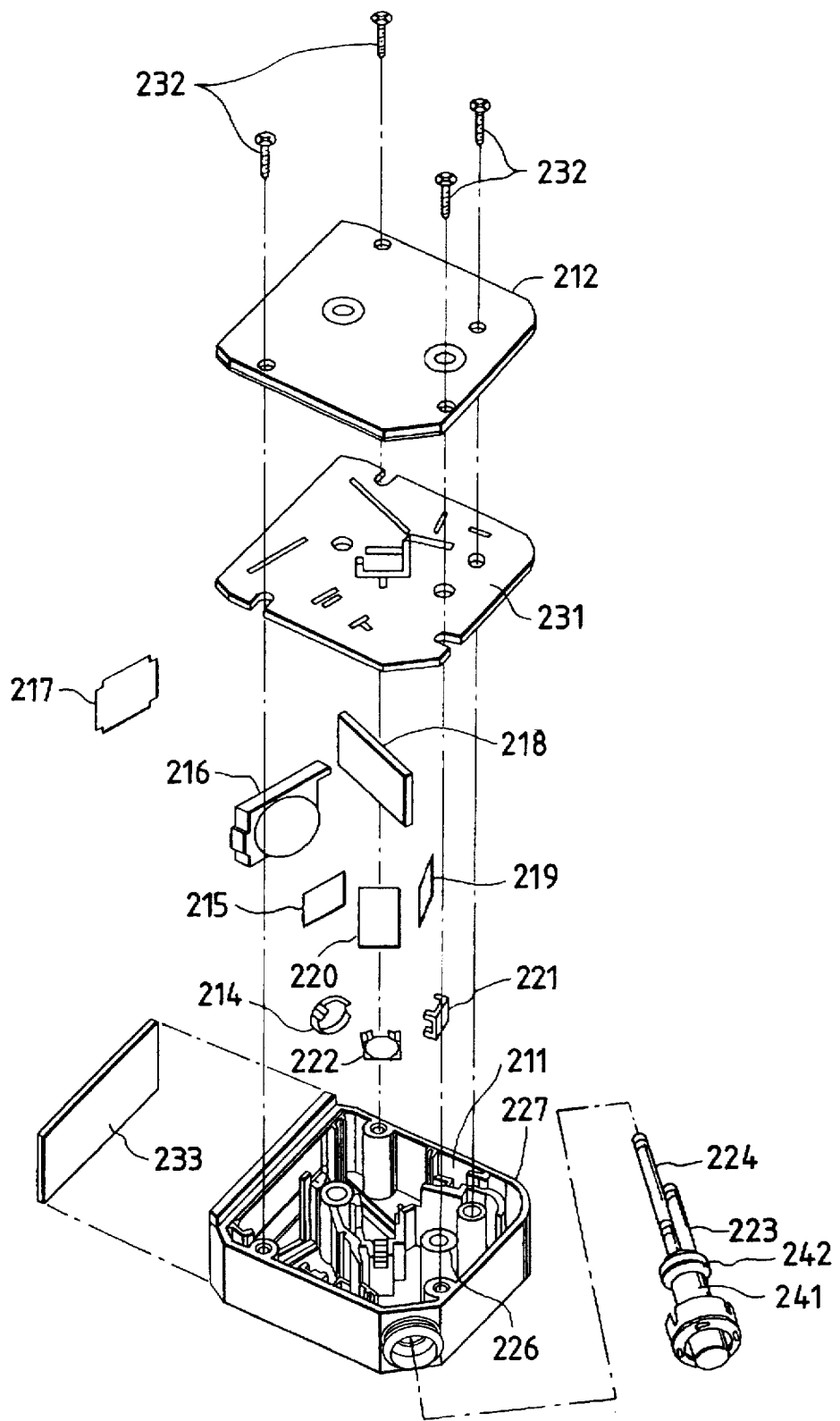
FIG. 22 is an exploded view of the head unit of FIGS. 21A–21C.

FIG. 19 is a vertical sectional view of a reflection-type photoelectric sensing apparatus according to this embodiment. FIG. 20 shows the entire configuration of the photoelectric sensing apparatus. FIGS. 21A–21C are a front view, a side view, and a top view of the photoelectric sensing apparatus. FIG. 22 is an exploded view of the photoelectric sensing apparatus. As shown in FIG. 20, the reflection-type photoelectric sensing apparatus consists of a head unit 201, an amplifier unit 202, and an optical fiber cable 203 and a connector 204 for connecting the units 201 and 202. The head unit 201 has an illuminating section for illuminating an object 205 to be detected, and light receiving sections for receiving resulting reflection light. The amplifier unit 202 has a light emitting element for emitting light to be supplied to the illuminating section, a signal processing circuit for judging the existence of the object 205 and its surface state such as glossiness, and a display section.

As shown in FIGS. 19 and 22, a case of the head unit 201 is composed of a base body 211 having an opening on one side and a cover body 212 for covering that opening. Light emitted from the light-emitting element such as a light-emitting diode (not shown) provided in the amplifier unit 202 is guided to the head unit 201 via an illuminating optical fiber 213 of the optical fiber cable 203. In the head unit 201, there are provided in the illumination light traveling direction a collimator lens 214 and a diffusing plate 215. An illuminating lens 216 and a polarizing filter 217 are disposed a given distance apart from the diffusing plate 215. S-polarization light or P-polarization light is applied from the illuminating lens 216 to an object detection area, resulting reflection light is separated by a polarizing beam splitter 218 in the receiving sections into two polarization components, which are input to a pair of light receiving sections. Polarizing filters 219 and 220 and receiving lenses 221 and 222 are provided in the respective light receiving sections. The P-polarization light and the S-polarization light are received by the respective photodetecting optical fibers 223 and 224.

Figure 23:
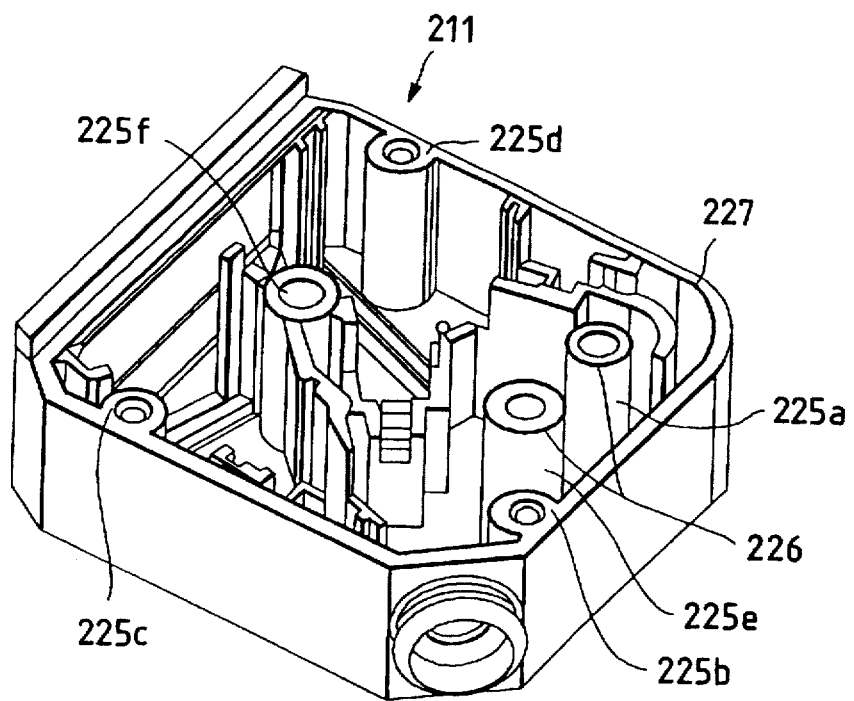
FIG. 23 is a perspective view showing a base body of the head unit of FIGS. 21A–21C.

As shown in FIG. 19, the above optical elements are incorporated in the base body 211 at prescribed positions. As shown in a perspective view of FIG. 23, the base body 211 is provided with protrusions for holding a number of optical elements, as well as support poles 225a–225f that are in contact with the inside face of the cover body 212 in an assembled state. Each of the support poles 225a–225f has an opening at the center. As shown in an enlarged view of FIG. 25, the end face of each of the support poles 225a, 225e and 225f in a central area is formed line protrusion 226 having a mountainous cross-section and surrounding the opening. The end face of the base body 211 is also formed with a line protrusion 227 having a mountainous cross-section and surrounding the opening. The line protrusions 226 and 227 have the same height.

Figure 24:
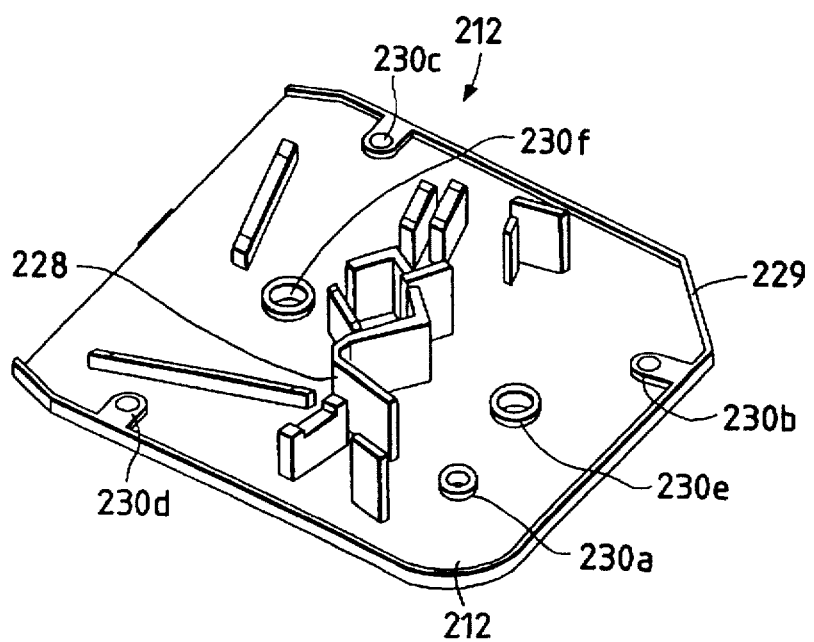
FIG. 24 is a perspective view showing the inside of a cover body of the head unit of FIGS. 21A–21C.

FIG. 24 is a perspective view showing the inside of the cover body 212. The cover body 212 holds the above-mentioned optical elements, and is formed with many light shielding protrusions 228. The cover body 212 is formed with a frame-like guide 229 at a peripheral portion. The cover body 212 is also formed with through holes and guides 230a–230f at positions corresponding to the support poles 225a–225f of the base body 211. The guide 129 and the guides 230a–230f have the same height, and are so formed as to be located adjacent to the line protrusions 226 and 227. As described later, the cover body 212 is fixed to the support poles 225a–225f of the base body 211 by, for instance, tapping screws through the guides 230a–230d.

After the optical elements are mounted on the base body 211, the cover body 212 is fixed thereto through a sealing rubber member 231. As shown in FIG. 22, the sealing rubber member 231 is a thin rubber member having many openings at positions corresponding to the protrusions 228 (provided on the inner face of the cover body 121) for light shielding and holding of the optical elements. The height of the guides 229, 230a, 230e and 230f, which are formed on the outer frame portion of the cover body 212 and at positions corresponding to the support poles 225a, 225e and 225f of the base body 211, is approximately the same as the thickness of the sealing rubber member 231.

Figure 25:
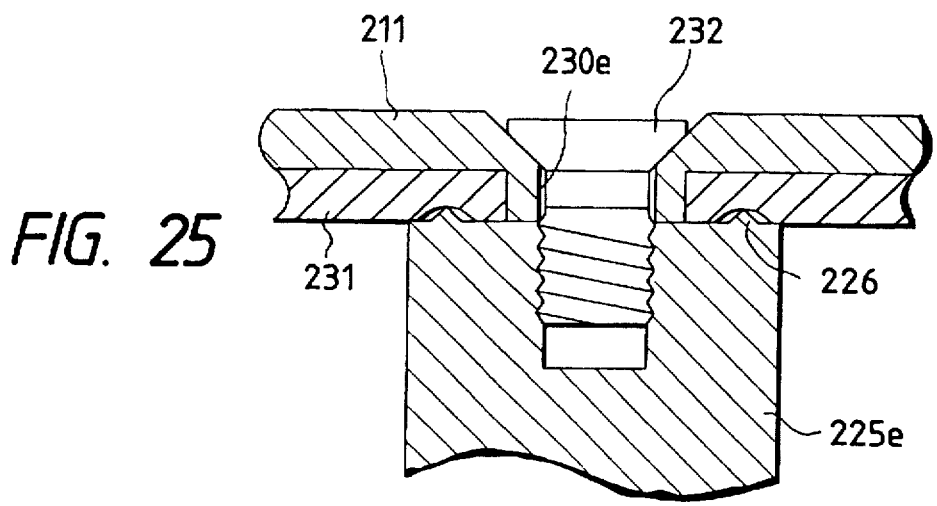
FIG. 25 is an enlarged sectional view showing how a support pole and the cover body are connected to each other.

After the optical elements and the optical fibers are mounted in the base body 211, the sealing rubber member 231 and the cover body 212 are placed thereon successively. In this state, the protrusions 228 of the cover body 212 penetrate the sealing rubber member 231 through its openings to thereby hold the optical elements, as well as come into the base body 211 to thereby serve as light shielding members, that is, restrict the path of light. Then, the cover body 212 is fixed to the base body 211 by the tapping screws 232, which are applied from above the cover body 212. In this state, referring to FIG. 25 that is an enlarged sectional view showing how the support pole 225e and the cover body 212 contact with each other, the line protrusion 26 formed on the end face of the support pole 225e contacts with the bottom face of the sealing rubber member 231, so that the cover body 212 is slightly lifted. In this state, if the tapping screws 232 are further rotated so that the cover body 212 is pressed against the sealing rubber member 231, the sealing rubber member 231 is deformed elastically to such an extent that the bottom face of the guide 230e contacts with the support pole 225e as shown in FIG. 25. Since the sealing rubber member 231 is deformed at the respective positions where the fastening is effected with the tapping screws, the inside of the head unit 201 can be kept hermetical, to thereby improve waterproofness.

A transparent plastic plate 233 is provided on the front side of the head unit 201 so as to cover its front portion. The transparent plastic plate 233 is connected to the head unit 201 by ultrasonic welding, to render the head unit 201 hermetical. Alternatively, the plate 233 may be fixed to the base body 211 through a sealing rubber member as in the case of the cover body 212.

Figure 26A:
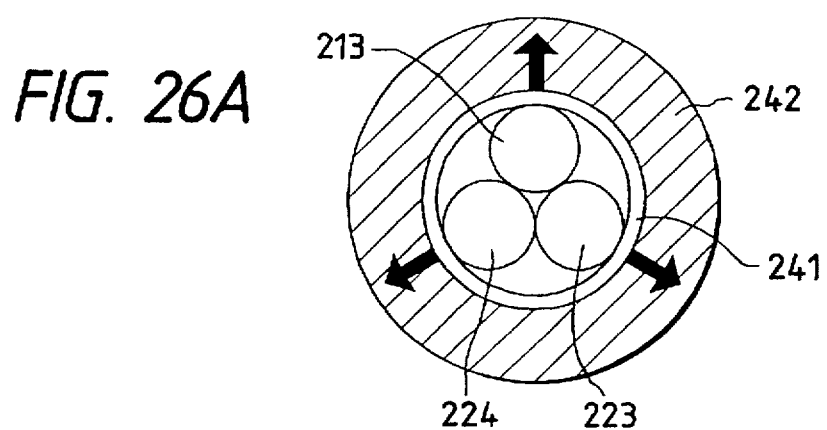
FIGS. 26A and 26B are sectional views showing optical fiber lead-out portion.
Figure 26B:
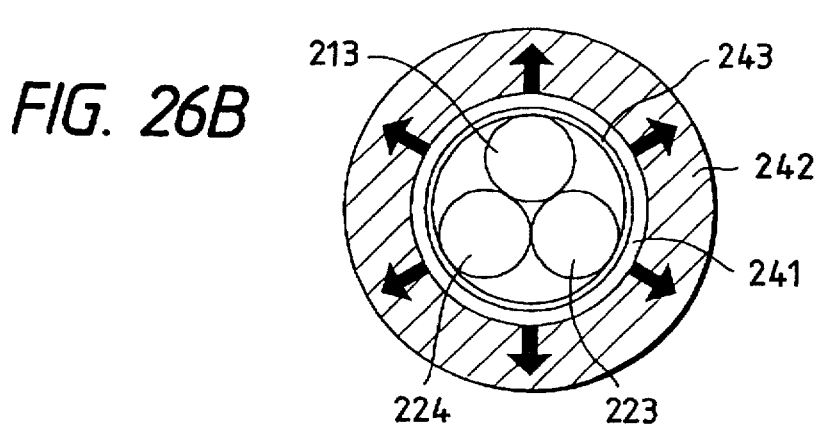

Next, a description will be made of how the optical fibers are attached to the head unit 201. FIG. 26A is a sectional view showing the optical fiber cable lead-out portion of the head unit 201. In this case, optical fibers 213, 223 and 224 are enclosed by a jacket 241, which is in turn covered with a rubber bush 242. The optical fibers 213, 223 and 224 are fixed to a cap of the head unit 201 by elastically deforming the rubber bush 242. With this structure, although outward force is exerted on the rubber bush 242 from the three optical fibers 213, 223 and 224 at the positions where the optical fibers contact with the jacket 241, no outward force is exerted from the portions between the above contact positions. Therefore, water likely goes into the head unit through those portions, resulting in insufficient waterproofness. In contrast, this embodiment employ a structure shown in FIG. 26B, in which the optical fibers 213, 223 and 224 are enclosed, over a limited axial length, by a cylindrical body such as a cylindrical metal pipe 243, which is covered with a jacket 241, which is in turn covered with a rubber bush 242. With this structure, as indicated by arrows in FIG. 26B, outward force is exerted on the rubber bush 242 from the entire circumference of the metal pipe 243 rather than from only the contact portions of the optical fibers 213, 223 and 224, to thereby elastically deform the rubber bush 242. In this case, no water goes into the head unit 201, and therefore the waterproofness can be improved.

The above embodiment is directed to the reflection-type photoelectric sensing apparatus in which light is guided to the head unit via the illuminating optical fiber, light having a given polarization direction is applied to an object, and reflection light beams from the object are received by a pair of light receiving sections, to thereby detect glossiness of the object. However, the invention can also be applied to a reflection-type photoelectric sensing apparatus for detecting the existence of an object by detecting reflection light from the object through a receiving lens.

As described above in detail, the invention not only facilitates assembling of the head unit because the optical elements can be mounted on the base body from one direction, but also allows the positioning of the optical elements correctly. Since the case of the head unit consists of the base body and the cover body, the number of parts can be reduced, which allows reduction in size and cost as well as stable detection of an object. Further, the head unit can be made hermetical, so that the waterproofness can be improved. In addition, the waterproofness of the optical fiber lead-out portion can be improved.

What is claimed is:

1. A photoelectric sensing apparatus comprising:

illuminating means for applying illumination light to a detection area of an object;

first and second photodetecting means for detecting first and second reflection light beams reflected from the object;

glossiness determining means for determining a glossiness of the object based on outputs of the first and second photodetecting means;

light quantity determining means for determining a light quantity of the object based on the outputs of the first and second photodetecting means;

evaluation function determining means for determining an evaluation function having at least one of a glossiness and a light quantity as a variable, said evaluation function being determined based on a previously determined glossiness difference and a previously determined light quantity difference between a detection sample object and a non-detection sample object;

threshold calculating means for calculating an object detection threshold based on values of the evaluation function for the detection sample object and the non-detection sample object; and object discriminating means for determining whether the object is an object to be detected by comparing a value of the evaluation function for the object with the object detection threshold.

2. The photoelectric sensing apparatus according to claim 1, wherein the evaluation function uses, as the variable, only the glossiness if the glossiness difference is larger than the light quantity difference by a first predetermined amount, uses only the light quantity if the light quantity difference is larger than the glossiness by a second predetermined amount, and otherwise uses both of the glossiness and the light quantity.

3. The photoelectric sensing apparatus according to claim 1, wherein the illumination light is linearly polarized light, and the first and second reflection light beams are S-polarization and P-polarization light beams, respectively.

* * * * *